United States Patent
Kuang et al.

(10) Patent No.: US 10,617,701 B2
(45) Date of Patent: *Apr. 14, 2020

(54) NUTRITIONAL COMPOSITIONS CONTAINING PHOSPHATIDYLETHANOLAMINE, SPHINGOMYELIN AND DOCOSAHEXAENOIC ACID

(71) Applicant: Mead Johnson Nutrition Company, Glenview, IL (US)

(72) Inventors: Chenzhong Kuang, Newburgh, IN (US); Dirk Hondmann, Winnetka, IL (US); Robert J. McMahon, Cincinnati, OH (US); Yan Xiao, Newburgh, IN (US)

(73) Assignee: MEAD JOHNSON NUTRITION COMPANY, Evansville, IN (US)

( * ) Notice: Subject to any disclaimer, the term of this patent is extended or adjusted under 35 U.S.C. 154(b) by 167 days.

This patent is subject to a terminal disclaimer.

(21) Appl. No.: 14/796,372

(22) Filed: Jul. 10, 2015

(65) Prior Publication Data

US 2017/0007629 A1 Jan. 12, 2017

(51) Int. Cl.
| | | |
|---|---|---|
| A61K 31/685 | (2006.01) | |
| A61K 38/40 | (2006.01) | |
| A61K 35/747 | (2015.01) | |
| A61K 31/688 | (2006.01) | |
| A61K 31/202 | (2006.01) | |
| A23C 9/152 | (2006.01) | |
| A23L 33/00 | (2016.01) | |
| A23L 33/12 | (2016.01) | |
| A23L 33/10 | (2016.01) | |

(52) U.S. Cl.
CPC ............ *A61K 31/685* (2013.01); *A23C 9/152* (2013.01); *A23C 9/1528* (2013.01); *A23L 33/00* (2016.08); *A23L 33/10* (2016.08); *A23L 33/12* (2016.08); *A23L 33/40* (2016.08); *A61K 31/202* (2013.01); *A61K 31/688* (2013.01); *A61K 35/747* (2013.01); *A61K 38/40* (2013.01); *A23V 2002/00* (2013.01); *A23V 2200/322* (2013.01); *A23V 2250/1848* (2013.01); *A23V 2250/1862* (2013.01); *A23V 2250/1868* (2013.01); *A23V 2250/54248* (2013.01)

(58) Field of Classification Search
None
See application file for complete search history.

(56) References Cited

U.S. PATENT DOCUMENTS

| | | |
|---|---|---|
| 4,791,193 A | 12/1988 | Okonogi et al. |
| 5,374,567 A | 12/1994 | Cartagena |
| 5,397,591 A | 3/1995 | Kyle |
| 5,550,156 A | 8/1996 | Kyle |
| 5,591,479 A | 1/1997 | Ponroy |
| 5,686,491 A | 11/1997 | Sherwood |
| 5,709,888 A | 1/1998 | Gil et al. |
| 5,849,885 A | 12/1998 | Nuyens |
| 5,861,491 A | 1/1999 | Nuijens |
| 5,919,913 A | 7/1999 | Nuyens |
| 6,500,472 B2 | 12/2002 | Uchida et al. |
| 6,620,326 B1 | 9/2003 | Lihme |
| 6,977,046 B2 | 12/2005 | Hubbuch |
| 7,354,896 B2 | 4/2008 | Kirwin et al. |
| 7,368,141 B2 | 5/2008 | Lihme |
| 7,812,138 B2 | 10/2010 | Lihme |
| 7,851,450 B2 | 12/2010 | Beerman et al. |
| 7,897,541 B2 | 3/2011 | Iwasaki et al. |
| 7,951,410 B2 | 5/2011 | McMahon et al. |
| 8,445,053 B2 | 5/2013 | Holst et al. |
| 2006/0286258 A1* | 12/2006 | Petschow ............. A61K 31/721 426/590 |
| 2008/0003330 A1* | 1/2008 | Rueda ................. A61K 31/202 426/72 |
| 2011/0009349 A1* | 1/2011 | Hodgkinson .......... A23D 9/007 514/25 |
| 2011/0293784 A1 | 12/2011 | Wittke |
| 2012/0276057 A1 | 11/2012 | Steenhout et al. |

(Continued)

FOREIGN PATENT DOCUMENTS

| | | |
|---|---|---|
| EP | 0183572 | 7/1992 |
| EP | 0484266 | 7/1992 |

(Continued)

OTHER PUBLICATIONS

Greenberg et al. "Omega-3 Fatty Acid Supplementation During Pregnancy" Reviews in Obstetrics & Gynecology, vol. 1, No. 4, 2008, p. 162-169.*
Fee et al. "Capture of lactoferrin and lactoperoxidase from raw whole milk by cation exchange chromatography" Separation and Purification Technology 48 (2006) 143-149.*
Yadomae, T., "Structure and biological activities of fungal beta-1,3-glucans." Yakugaku Zasshi. 2000;120:413-431.
Awad, K., et al., "Effects of exercise and nutritional intake on sleep architecture in adolescents," Sleep Breath. Mar. 2013; 17(1): 117-124.
Bemiller, J., "An Introduction to Pectins: Structure and Properties," Chemistry and Function of Pectins; Chapter 1; 1986.
Brenna, J., "Efficiency of conversion of a-linolenic acid to long chain n-3 fatty acids in man," Current Opinion in Clinical Nutrition and Metabolic Care 2002, 5:127-132.

(Continued)

*Primary Examiner* — Thane Underdahl
(74) *Attorney, Agent, or Firm* — Troutman Sanders LLP; Ryan Schneider; Chris Davis

(57) ABSTRACT

The present disclosure provides a composition and method for promoting functional neuronal development in pediatric subjects. The composition comprises in some embodiments up to about 7 g/100 Kcal of a fat or lipid source; up to about 5 g/100 Kcal of a protein source; about 3 mg/100 Kcal to about 50 mg/100 Kcal of phosphatidylethanolamine; about 0.15 mg/100 Kcal to about 75 mg/100 Kcal of sphingomyelin; and about 5 mg/100 Kcal to about 75 mg/100 Kcal of docosahexaenoic acid. The methods comprise, in some embodiments, administering the aforementioned composition to a pediatric subject.

16 Claims, 3 Drawing Sheets

(56) References Cited

U.S. PATENT DOCUMENTS

| | | |
|---|---|---|
| 2013/0071446 A1 | 3/2013 | Van Der Beek et al. |
| 2013/0150306 A1 | 6/2013 | Wittke |
| 2014/0199265 A1 | 7/2014 | Kuang et al. |
| 2015/0023923 A1 | 1/2015 | Kuang et al. |
| 2015/0037455 A1 | 2/2015 | Chichlowski et al. |

FOREIGN PATENT DOCUMENTS

| | | | |
|---|---|---|---|
| EP | 0433113 | | 5/1995 |
| EP | 2046149 | | 11/2010 |
| EP | 2251030 | | 11/2010 |
| EP | 2251031 | | 11/2010 |
| EP | 2258216 | | 12/2010 |
| EP | 2258217 | | 12/2010 |
| EP | 2594282 | | 5/2013 |
| WO | 1992000799 | | 1/1992 |
| WO | 1997017132 | | 5/1997 |
| WO | 2002018237 | | 3/2002 |
| WO | 2011069987 | | 6/2011 |
| WO | 2011115476 | | 9/2011 |
| WO | WO2014109862 | * | 7/2014 |
| WO | 2015086169 | | 6/2016 |

OTHER PUBLICATIONS

Droro, D., et al., "Effect of vitamin B12 deficiency on neurodevelopment in infants: current knowledge and possible mechanisms," Nutr Rev. 2008, 66: 250-255.

Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, Aug. 2005.

Fenzl, T., et al., "Sleep disturbances in highly stress reactive mice: Modeling endophenotypes of major depression," BMC Neuroscience 2011, 12:29.

Garcia, C., et al., "Phospholipid fingerprints of milk from different mammalians determined by 31P NMR: towards specific interest in human health," Food Chem. 2012, 135: 1777-1778.

Gurnida, D., et al., "Association of complex lipids containing gangliosides with cognitive development of 6-month-old infants," Early Human Development (2012).

Herlenius, E., et al., "Development of neurotransmitter systems during critical periods," Experimental Neurology 190 (2004) S8-S21.

Ibfan "Breastfeeding and Brain Development (Cognitive Development)", Information Sheet-9, IBFAN Asia Pacific/Breastfeeding Promotion Network of India (BPNI), Feb. 2005, p. 1-2.

Kamemori, N., et al., "Trans-Endothelial and Trans-Epithelial Transfer of Lactoferrin in the Brain through BBB and BCSFB in Adult Rats," J. Vet. Med. Sci. 70(3): 313-315, 2008.

Kuhara, T., et al., "Oral Administration of Lactoferrin Increases NK Cell Activity in Mice via Increased Production of IL-18 and Type I IFN in the Small Intestine," Journal of Interferon & Cytokine Research 26:489-499 (2006).

Kunz, et al., Oligosaccharides in Human Milk: Structure, Functional, and Metabolic Aspects, Ann. Rev. Nutr. 20: 699-722 (2000).

Ling, J., et al.. "Perspectives on Interactions Between Lactoferrin and Bacteria," Biochemistry and Cell Biology, pp. 275-281 (2006).

Lonnerdal, B., "Nutritional roles of lactoferrin," Curr Opin Clin Nutr Metal Care. 2009, 12: 1363-1950.

Lopez, C., et al., "Human milk fat globules: Polar lipid composition and in situ structural investigations revealing the heterogeneous distribution of proteins and the lateral segregation of sphingomyelin in the biological membrane," Colloids and Surfaces B: Biointerfaces 83 (2011) 29-41.

Martinez, M., "Tissue levels of polyunsaturated fatty acids during early human development," J. Pediatr 1992;120: S129-38.

Martinez, M., et al., "Fatty Acid Composition of Human Brain Phospholipids During Normal Development," J. Neurochem. 71, 2528-2533 (1998).

Mather, I., "A Review and Proposed Nomenclature for Major Proteins of the Milk-Fat Globule Membrane1,2," 2000 J Dairy Sci 83: 203-247.

McJarrow, P., et al., "Influence of dietary gangliosides on neonatal brain development," Nutrition Reviews vol. 67 (8):451-463.

Menard, O., et al., "Buffalo vs. cow milk fat globules: Size distribution, zeta-potential, compositions in total fatty acids and in polar lipids from the milk fat globule membrane," Food Chemistry 120 (2010) 544-551.

Mintel, "Golden Growing-Up Formula Goat Milk Powder," Database Accession No. 1694223, Jan. 2012 XP002730875.

Mintel, "Growing-Up Milk Powder (Stage 3) with Lactoferrin," Database Accession No. 2081489, Jan. 2012 XP002730876.

Mintel, "Growing-Up Milk for Children," Database Accession No. 2085763, Jun. 2013 XP002730877.

Mintel, "New Birth Formula," Database Accession No. 1249000, Jan. 2010 XP002673470.

Mintel, "Stage 2 Infant Formula," Database Accession No. 2032623, Mar. 2013 XP002730874.

Monaco, M., et al., "Addition of Polydextrose and Galactooligosaccharide to Formula Does Not Affect Bacterial Translocation in the Neonatal Piglet," JPGN 2011;52: 2010-216.

Morgan, B. L., et al., "Effects of environmental stimulation on brain N-acetylneuraminic acid content and behavior." J Nutr 110(3): 425-432, 1980.

Morgan, B., et al., "Effects of Administration of N-Acetylneuraminic Acid (NANA) on Brain NANA Content and Behavior," J. Nutr. 110: 416-424, 1980.

Mulder, A., et al., "Bovine lactoferrin supplementation supports immune and antioxidant status in healthy human males," Nutrition Research 28 (2008) 583-589.

Ochoa, T., et al., "Impact of Lactoferrin Supplementation on Growth and Prevalence of Giardia Colonization in Children," Brief Report CID 2008:46 (Jun. 15).

Precht, D., et al., "C18:1, C18:2 and C18:3 trans and cis fatty acid isomers including conjugated cis 9, trans 11 linoleic acid (CLA) as well as total fat composition of German human milk lipids," Nahrung, 43 (4): 233-244. 1999.

Rahman, M.D., M. et al., "Growth promotion and cell binding ability of bovine lactoferrin to Bifidobacterium longum," Anaerobe, 15(4): 133-137.

Rai, D., et al., "Longitudinal Changes in Lactoferrin Concentrations in Human Milk: A Global Systematic Review," Crit Rev Food Sci & Nutr, 54:12, 1539-1547.

Ribeiro, T., et al., "Stool Pattern Changes in Toddlers Consuming a Follow-on Formula Supplemented With Polydextrose and Galactooligosaccharides," JPGN 2012;54: 288-290.

Salvini, F., et al., "A Specific Prebiotic Mixture Added to Starting Infant Formula Has Long-Lasting Bifidogenic Effects1-3," J. Nutr. 141: 1335-1339, 2011.

Savino, F., et al., "Lactobacillus reuteri DSM 17 938 in Infantile Colic: A Randomized, Double-Blind, Placebo-Controlled Trial," Pediatrics published online Aug. 16, 2010; DOI 10.1542/peds.2010-0433.

Scalabrin, D., et al., "New Prebiotic Blend of Polydextrose and Galacto-oligosaccharides Has a Bifidogenic Effect in Young Infants," JPGN 2012;54: 343-352.

Svennerholm, L., et al., "Chromatographic Separation of Human Brain Gangliosides," Journal of Neurochemistry, 1963, vol. 10, pp. 613-623.

Thomas, C., et al., "Histamine Derived from Probiotic Lactobacillus reuteri Suppresses TNF via Modulation of PKA and ERK Signaling," PLoS ONE 7(2):2012.

Timby, N., et al., "Neurodevelopment, nutrition, and growth until 12 mo of age in infants fed a low-energy, low-protein formula supplemented with bovine milk fat globule membranes: a randomized controlled trial1-3," Am J Clin Nutr 2014;99:860-868.

Veereman-Wauters, G., et al., "Milk fat globule membrane (INPULSE) enriched formula milk decreases febrile episodes and may improve behavioral regulation in young children," Nutrition 28 (2012) 749-752.

Veereman-Wauters, G., et al., "Physiological and Bifidogenic Effects of Prebiotic Supplements in Infant Formulai," JPGN 2011;52: 763-771.

(56) References Cited

OTHER PUBLICATIONS

Zavaleta, N., et al., "Efficacy of an MFGM-enriched Complementary Food in Diarrhea, Anemia, and Micronutrient Status in Infants," JPGN 2011;53: 561-568.

Ziegler, E., et al., "Term Infants Fed Formula Supplemented With Selected Blends of Prebiotics Grow Normally and Have Soft Stools Similar to Those Reported for Breast-fed Infants," Journal of Pediatric Gastroenterology and Nutrition 44:359-364 (2007).

* cited by examiner

NUTRITIONAL COMPOSITIONS CONTAINING PHOSPHATIDYLETHANOLAMINE, SPHINGOMYELIN AND DOCOSAHEXAENOIC ACID

TECHNICAL FIELD

The present disclosure relates generally to nutritional compositions that are suitable for administration to pediatric subjects or pregnant or lactating females. In some embodiments, the nutritional composition comprises phosphatidylethanolamine, sphingomyelin, and docosahexaenoic acid. In some other embodiments, the nutritional composition further comprises lactoferrin. Furthermore, the disclosure relates to methods for promoting functional neuronal maturation in pediatric subject via administration of the nutritional composition of the present disclosure.

BACKGROUND ART

Polar lipids are constituent components of some foods, although their quality and quantity vary considerably depending on the food source. Dairy products such as milk and eggs are the richest sources of these polar lipids; the glycerophospholipids are also present in plants such as soybean. Nevertheless, a pediatric subject may need to consume a large amount of bovine milk (~2,000 ml) to obtain a reasonable amount of polar lipids. In addition, consumption of eggs is also limited in infants and children due to the possibility of allergic reactions to the proteins in eggs. Plants are not a source of some of the polar lipids and in particular gangliosides because they are unable to synthesize sialic acid, a component of gangliosides. Furthermore the quality of polar lipids in plants is totally different than milk polar lipids not only due to the fatty acid profile but also due to the ratio of the individual phospholipid components of these lipids.

Polar lipids, especially those found in milk, are composed of three major groups of lipids:
  (i) Glycerophospholipids such as phosphatidylcholine (PC), phosphatidylethanolamine (PE), phosphatidylserine (PS), and phosphatidylinositol (PI), and their derivatives.
  (ii) Sphingoids or sphingolipids such as sphingomyelin (SM) and glycosphingolipids comprising cerebrosides (neutral glycosphingolipids containing uncharged sugars) and the gangliosides (GG, acidic glycosphingolipids containing sialic acid) and their derivatives.
  (iii) Cholesterol and its derivatives.

Phosphatidylethanolamine is a phospholipid found in biological membranes, particularly in nervous tissue such as the white matter of brain, nerves, neural tissue, and in spinal cord, where they make up 45% of all phospholipids. Sphingomyelin (SM) is a type of sphingolipid found in animal cell membranes, especially in the membranous myelin sheath that surrounds some nerve cell axons. It usually consists of phosphocholine and ceramide, or a phosphoethanolamine head group; therefore, sphingomyelins can also be classified as sphingophospholipids. In humans, SM represents ~85% of all sphingolipids, and typically makes up 10-20 mol % of plasma membrane lipids. Sphingomyelins are present in the plasma membranes of animal cells and are especially prominent in myelin, a membranous sheath that surrounds and insulates the axons of some neurons.

Lactoferrin (LF), an iron-binding glycoprotein, is one of the major multifunctional agents present in human milk. It has the capacity to bind two molecules of iron in a reversible fashion and can facilitate the uptake of iron within the intestines. Further, lactoferrin has been shown to be both bacteriostatic and bactericidal, and it aids in preventing intestinal infections in humans, especially in pediatric subjects. Additionally, human lactoferrin appears to have a positive effect on the symptoms of diarrheal diseases.

Docosahexaenoic acid (DHA) is an omega-3 fatty acid that is a primary structural component of the human brain, cerebral cortex, skin, sperm, testicles and retina. It can be synthesized from alpha-linolenic acid or obtained directly from maternal milk or fish oil. DHA is the most abundant omega-3 fatty acid in the brain and retina. DHA comprises 40% of the polyunsaturated fatty acids (PUFAs) in the brain and 60% of the PUFAs in the retina. Fifty percent of the weight of a neuron's plasma membrane is composed of DHA. DHA is richly supplied during breastfeeding, and DHA levels are high in breastmilk. DHA concentrations in breast milk range from 0.07% to greater than 1.0% of total fatty acids, with a mean of about 0.34%. DHA levels in breast milk are higher if a mother's diet is high in fish. DHA has recently gained attention as a supplement for pregnant women, noting studies of improved attention and visual acuity in children of mothers given DHA during pregnancy. Nevertheless, the majority of pregnant women in the U.S. fail to get the recommended amount of DHA in their diets. A working group from the International Society for the Study of Fatty Acids and Lipids recommended 300 mg/day of DHA for pregnant and lactating women, whereas the average consumption was between 45 mg and 115 mg per day of the women in the study.

Human milk contains a number of components that contribute to the growth and development of the brain in infants. But, cow's milk and many commercially available infant formulas that are based on cow's milk provide only trace amounts of polyunsaturated fatty acids, such as DHA, lactoferrin and polar lipids. Therefore, there is a need to provide a formula matrix that mimics the qualities of human milk by allowing for effective supplementation of lipids and proteins in order to optimize brain growth and development in formula fed infants.

More specifically, there is a need for nutritional compositions that further promote brain development in pediatric subjects. The present disclosure meets this need by providing nutritional compositions comprising the milk polar lipids phosphatidylethanolamine and sphingomyelin along with lactoferrin and docosahexaenoic acid. The present compositions advantageously promote neuronal maturation in pediatric subjects.

BRIEF SUMMARY

Briefly, the present disclosure is directed to compositions and methods for supporting and promoting functional neuronal maturation in pediatric subjects. The compositions comprise phosphatidylethanolamine, sphingomyelin, lactoferrin and docosahexaenoic acid. More particularly, in certain embodiments, a nutritional composition comprises:
  up to about 7 g/100 Kcal of a fat or lipid;
  up to about 5 g/100 Kcal of a protein source;
  about 3 mg/100 Kcal to about 50 mg/100 Kcal of phosphatidylethanolamine;
  about 0.15 mg/100 Kcal to about 75 mg/100 Kcal of sphingomyelin; and
  about 5 mg/100 Kcal to about 75 mg/100 Kcal of docosahexaenoic acid.

In some embodiments, the nutritional composition of the present disclosure further comprises about 10 mg/100 Kcal to about 200 mg/100 Kcal of lactoferrin.

In other embodiments, the disclosure is directed to methods for promoting neuronal maturation in a pediatric subject by administering to the subject the aforementioned nutritional composition. The pediatric subject may be an infant or a child, and the nutritional composition may be provided as an infant formula or growing up milk.

The present disclosure further provides maternal supplements comprising phosphatidylethanolamine; sphingomyelin; lactoferrin; and docosahexaenoic acid. The maternal supplements may be used by pregnant or lactating mothers to promote neuronal maturation in a fetus or a breast-fed infant, respectively.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Figure 1:
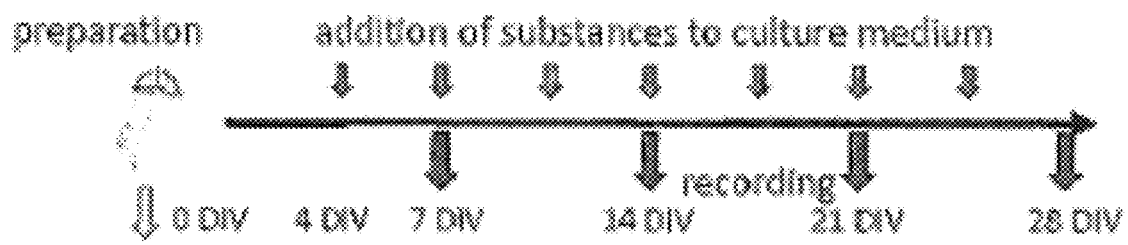
FIG. 1 is a graph depicting the time points for recording activity during four weeks of functional neuronal maturation and the time points for addition of substances to the culture medium. Specifically, embryonic mouse cortical cells growing on microelectrode arrays and treated with various combinations of PE, SM, LF and DHA.

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure relates generally to nutritional compositions, especially milk-based nutritional compositions that are suitable for administration to a pediatric subject. Additionally, the disclosure relates to methods of promoting functional neuronal maturation in a pediatric subject via administration of the nutritional compositions. The present disclosure also relates to nutritional supplements for pregnant and lactating women and methods of promoting functional neuronal maturation in fetuses or breast fed infants.

"Nutritional composition" means a substance or formulation that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

"Pediatric subject" means a human no greater than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or full term) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, extremely low birth weight infants and preterm infants. "Preterm" means an infant born before the end of the $37^{th}$ week of gestation. "Late preterm" means an infant form between the $34^{th}$ week and the $36^{th}$ week of gestation. "Full term" means an infant born after the end of the $37^{th}$ week of gestation. "Low birth weight infant" means an infant born weighing less than 2500 grams (approximately 5 lbs, 8 ounces). "Very low birth weight infant" means an infant born weighing less than 1500 grams (approximately 3 lbs, 4 ounces). "Extremely low birth weight infant" means an infant born weighing less than 1000 grams (approximately 2 lbs, 3 ounces).

"Child" means a subject ranging in age from 12 months to 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

"Maternal supplement" refers to a composition formulated for administration to a pregnant or lactating female. A maternal supplement may be provided in the form of a pill or tablet or may be provided as a functional food or beverage.

The term "degree of hydrolysis" refers to the extent to which peptide bonds are broken by a hydrolysis method.

The term "partially hydrolyzed" means having a degree of hydrolysis which is greater than 0% but less than about 50%.

The term "extensively hydrolyzed" means having a degree of hydrolysis which is greater than or equal to about 50%.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Probiotic" means a microorganism with low or no pathogenicity that exerts a beneficial effect on the health of the host.

The term "inactivated probiotic" means a probiotic wherein the metabolic activity or reproductive ability of the referenced probiotic has been reduced or destroyed. The "inactivated probiotic" does, however, still retain, at the cellular level, its cell structure or other structure associated with the cell, for example exopolysaccharide and at least a portion its biological glycol-protein and DNA/RNA structure. As used herein, the term "inactivated" is synonymous with "non-viable".

"Prebiotic" means a non-digestible food ingredient that beneficially affects the host by selectively stimulating the growth and/or activity of one or a limited number of bacteria in the digestive tract that can improve the health of the host.

"Polar lipids" are the main constituents of natural membranes, occurring in all living organisms. The polar lipids in milk (i.e., milk polar lipids) are mainly situated in the milk fat globule membrane (MFGM). This is a highly complex biological membrane that surrounds the fat globule, hereby stabilizing it in the continuous phase of the milk. Polar lipids are also present in sources other than milk such as eggs, meat and plants.

Polar lipids are generally divided into phospholipids and sphingolipids (including gangliosides), which are amphiphilic molecules with a hydrophobic tail and a hydrophilic head group. The glycerophospholipids consist of a glycerol backbone on which two fatty acids are esterified on positions sn-1 and sn-2. These fatty acids are more unsaturated than the triglyceride fraction of milk. On the third hydroxyl, a phosphate residue with different organic groups (choline, serine, ethanolamine, etc.) may be linked. Generally, the fatty acid chain on the sn-1 position is more saturated compared with that at the sn-2 position. Lysophospholipids contain only one acyl group, predominantly situated at the sn-1 position. The head group remains similar. The characteristic structural unit of sphingolipids is the sphingoid base, a long-chain (12-22 carbon atoms) aliphatic amine containing two or three hydroxyl groups. Sphingosine (d18:1), is the most prevalent sphingoid base in mammalian sphingolipids, containing 18 carbon atoms, two hydroxyl groups and one double bond. A ceramide is formed when the amino group of this sphingoid base is linked with, usually, a saturated fatty acid. On this ceramide unit, an organophosphate group can be bound to form a sphingophospholipid (e.g., phosphocholine in the case of sphingomyelin) or a saccharide to form the sphingoglycolipids (glycosylceramides). Monoglycosylceramides, like glucosylceramide or galactosylceramide are often denoted as cerebrosides while tri- and tetraglycosylceramides with a terminal galactosamine residue are denoted as globosides. Finally, gangliosides are highly complex oligoglycosylceramides, containing one or more sialic acid groups in addition to glucose, galactose and galactosamine.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

As used herein, "lactoferrin from a non-human source" means lactoferrin which is produced by or obtained from a source other than human breast milk. For example, lactoferrin for use in the present disclosure includes human lactoferrin produced by a genetically modified organism as well as non-human lactoferrin. The term "organism", as used herein, refers to any contiguous living system, such as animal, plant, fungus or micro-organism. Exemplary non-human sourced lactoferrin includes bovine lactoferrin.

As used herein, "non-human lactoferrin" means lactoferrin that has an amino acid sequence that is different than the amino acid sequence of human lactoferrin.

"Modulate" or "modulating" means exerting a modifying, controlling and/or regulating influence. In some embodiments, the term "modulating" means exhibiting an increasing or stimulatory effect on the level/amount of a particular component. In other embodiments, "modulating" means exhibiting a decreasing or inhibitory effect on the level/amount of a particular component.

All percentages, parts and ratios as used herein are by weight of the total formulation, unless otherwise specified.

All amounts specified as administered "per day" may be delivered in one unit dose, in a single serving or in two or more doses or servings administered over the course of a 24 hour period.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The present disclosure is generally directed to pediatric nutritional compositions, such as milk-based nutritional compositions, and maternal supplements comprising PE, SM and DHA and to uses thereof. In certain embodiments, the compositions further comprise LF. The nutritional compositions of the present disclosure advantageously support brain development in pediatric human subjects, such as an infant (preterm and/or term) or a child. The nutritional compositions of the present disclosure more specifically promote neuronal maturation in pediatric subjects.

Nutrition during gestation, infancy and childhood has an impact on early brain development. Accordingly, the nutritional composition of the present disclosure supports healthy brain development and specifically neuronal maturation.

Thus, in some embodiments, the present disclosure is directed to a method for promoting early brain development, while in more particular embodiments the present disclosure is directed to a method for promoting neuronal maturation, more specification, functional neuronal maturation. The present method comprises administering a composition comprising the polar lipids PE and SM along with DHA and, in some embodiments, LF. While not being bound by theory, it is believed that the combination of PE, SM, LF and DHA acts synergistically in promoting neuronal maturation.

In further embodiments, the present compositions comprise prebiotics, especially PDX and GOS. While not being bound by theory, it is believed that PDX and GOS alter the production of biogenic amines and neurotransmitters within the central nervous system, and such changes may explain the beneficial effects of feeding PDX/GOS on social skills, anxiety and memory functions. It is therefore believed that PDX/GOS may act synergistically with the PE, SM, LF and DHA used in the present compositions to further enhance brain development and promote neuronal maturation. In summary, the disclosed nutritional composition may play an important role during infancy and childhood by modifying intestinal microflora, optimizing brain composition, and improving a variety of brain-related behaviors and functions.

PE is present in the nutritional composition in an amount ranging from about 3 mg/100 Kcal to about 50 mg/100 Kcal. In some embodiments, PE is present in an amount of about 3.7 mg/100 Kcal to about 37 mg/100 Kcal, and in further embodiments, the PE is present in an amount ranging from about 5 mg/100 Kcal to about 25 mg/100 Kcal.

Sphingomyelin is present in the nutritional composition in an amount ranging from about 0.15 mg/100 Kcal to about 75 mg/100 Kcal. In some embodiments, the sphingomyelin is present in an amount ranging from about 3 mg/100 Kcal to about 30 mg/100 Kcal, or about 10 mg/100 Kcal to about 20 mg/100 Kcal.

The sphingomyelin and phosphatidylethanolamine may be provided by any source. In particular embodiments, the sphingomyelin and phosphatidylethanolamine are provided by a milk product enriched in such phospholipids, such as products that are enriched in MFGM. An MFGM-enriched whey protein concentrate is commercially available, for example, from ARLA Foods as Lacprodan® MFGM-10, and provides a suitable source of phosphatidylethanolamine and sphingomyelin for the present compositions. The source of phosphatidylethanolamine and/or sphingomyelin may advantageously comprise additional polar milk lipids, including but not limited to glycerophospholipids such as phosphatidylcholine (PC), phosphatidylserine (PS), and phosphatidylinositol (PI), and their derivatives; other sphingoids; glycosphingolipids including of cerebrosides; gangliosides (GG, acidic glycosphingolipids containing sialic acid) and their derivatives; and cholesterol and its derivatives. These additional milk polar lipids also may be sourced from an MFGM-enriched ingredient, such as an MFGM-enriched whey protein concentrate. While not being bound by theory, it is believed that these additional milk polar lipids are also beneficial to brain development and may act synergistically with PE, SM, LF and DHA.

As discussed above, the nutritional compositions may also comprise lactoferrin. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR) and 28 to 31 (RKVR) are arginine-rich cationic domains in the N-terminus especially critical to the antimicrobial activities of lactoferrin. A similar region in the N-terminus is found in bovine lactoferrin (residues 17 to 42; FKCRRWQWRMKKLGAPSITCVRRAFA).

As described in "*Perspectives on Interactions Between Lactoferrin and Bacteria*" (BIOCHEMISTRY AND BIOLGY, pp 275-281 (2006)), lactoferrins from different host species may vary in their amino acid sequences though commonly possess a relatively high isoelectric point with positively charged amino acids at the end terminal region of the internal lobe. Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 55% homology with human lactoferrin and in some embodiments, at least 65% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin. In particular embodiments, the lactoferrin is bLF.

In one embodiment, lactoferrin is present in the nutritional composition in an amount ranging from about 10 mg/100 Kcal to about 200 mg/100 Kcal. In certain embodiments, the lactoferrin is present in an amount ranging from about 15 mg/100 Kcal to about 100 mg/150 Kcal. In still another embodiment, particularly where the nutritional composition is an infant formula, the lactoferrin is present in the nutritional composition in an amount ranging from about 60 mg/100 Kcal to about 150 mg/100 Kcal or about 60 mg/100 Kcal to about 100 mg/100 Kcal.

The bLF that is used in certain embodiments may be any bLF isolated from whole milk and/or having a low somatic cell count, wherein "low somatic cell count" refers to a somatic cell count less than 200,000 cells/mL. By way of example, suitable bLF is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Lactoferrin for use in the present disclosure may be, for example, isolated from the milk of a non-human animal or produced by a genetically modified organism. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof. n some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The nutritional composition of the disclosure also contains DHA. DHA is present, in some embodiments, in an amount ranging from about 5 mg/100 Kcal to about 75 mg/100 Kcal, more preferably about 10 mg/00 Kcal to about 50 mg/100 Kcal. The DHA may be provided from any source of LCPUFAs. Other suitable LCPUFAs that may be present in certain embodiments of the present compositions include, but are not limited to, α-linoleic acid, γ-linoleic acid, linoleic acid, linolenic acid, eicosapentaenoic acid (EPA) and arachidonic acid (ARA).

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

The source of DHA and ARA, when present, may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

The nutritional composition may also contain one or more prebiotics (also referred to as a prebiotic component) in certain embodiments. Prebiotics exert health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.01 g/100 Kcal to about 0.15 g/100 Kcal. In certain embodiments, the total amount of prebiotics present in the nutritional composition may be from about 0.03 g/100 Kcal to about 0.07 g/100 Kcal. Moreover, the nutritional composition may comprise a prebiotic component comprising PDX. In some embodiments, the prebiotic component comprises at least 20% w/w PDX, GOS or a mixture thereof.

If PDX is used in the prebiotic composition, the amount of PDX in the nutritional composition may, in an embodiment, be within the range of from about 0.015 g/100 Kcal to about 0.15 g/100 Kcal. In another embodiment, the amount of polydextrose is within the range of from about 0.02 g/100 Kcal to about 0.06 g/100 Kcal. In some embodiments, PDX may be included in the nutritional composition in an amount sufficient to provide between about 1.0 g/L and 10.0 g/L. In another embodiment, the nutritional composition contains an amount of PDX that is between about 2.0 g/L and 8.0 g/L. And in still other embodiments, the amount of PDX in the nutritional composition may be from about 0.015 g/100 Kcal to about 0.05 g/100 Kcal.

In other embodiments, the prebiotic component may comprise GOS. If GOS is used in the prebiotic composition, the amount of GOS in the nutritional composition may, in an embodiment, be from about 0.015 g/100 Kcal to about 0.15 g/100 Kcal. In another embodiment, the amount of GOS in the nutritional composition may be from about 0.02 g/100 Kcal to about 0.05 g/100 Kcal. In other embodiments, the amount of GOS in the nutritional composition may be from about 0.015 g/100 Kcal to about 0.1 g/100 Kcal or from about 0.01 mg/100 Kcal to about 0.05 mg/100 Kcal.

In a particular embodiment of the present invention, PDX is administered in combination with GOS. In a particular embodiment, GOS and PDX are supplemented into the nutritional composition in a total amount of at least about 0.02 g/100 Kcal or about 0.02 g/100 Kcal to about 0.15 mg/100 Kcal. In some embodiments, the nutritional composition may comprise GOS and PDX in a total amount of from about 0.06 to about 0.08 mg/100 Kcal.

It is further believed that PDX and GOS have beneficial effect on brain development via the gut-brain-immune axis and therefore, when present, act synergistically to enhance brain development, and particularly, neuronal maturation.

In a further embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (LGG) (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1 \times 10^4$ to about $1.5 \times 10^{12}$ cfu of probiotic(s) per 100 Kcal. In some embodiments the amount of probiotic may be from about $1 \times 10^6$ to about $1 \times 10^9$ cfu of probiotic(s) per 100 Kcal. In certain other embodiments the amount of probiotic may vary from about $1 \times 10^7$ cfu/100 Kcal to about $1 \times 10^8$ cfu of probiotic(s) per 100 Kcal. In particular embodiments, the probiotic is LGG.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

In some embodiments, the nutritional composition may include a source comprising probiotic cell equivalents, which refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc. In non-viable probiotics are included in the nutritional composition, the amount of the probiotic cell equivalents may vary from about $1\times10^4$ to about $1.5\times10^{10}$ cell equivalents of probiotic(s) per 100 Kcal. In some embodiments the amount of probiotic cell equivalents may be from about $1\times10^6$ to about $1\times10^9$ cell equivalents of probiotic(s) per 100 Kcal nutritional composition. In certain other embodiments the amount of probiotic cell equivalents may vary from about $1\times10^7$ to about $1\times10^8$ cell equivalents of probiotic(s) per 100 Kcal of nutritional composition.

In some embodiments, the probiotic source incorporated into the nutritional composition may comprise both viable colony-forming units, and non-viable cell-equivalents. In particular embodiments, the probiotic is LGG.

In some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅚ of the time elapsed in the exponential phase.

The nutritional compositions of the disclosure may comprise at least one protein source, in addition to the LF. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In some embodiments, the proteins of the nutritional composition are provided as intact proteins. In other embodiments, the proteins are provided as a combination of both intact proteins and hydrolyzed proteins. In certain embodiments, the proteins may be partially hydrolyzed or extensively hydrolyzed. In still other embodiments, the protein source comprises amino acids. In yet another embodiment, the protein source may be supplemented with glutamine-containing peptides. In another embodiment, the protein component comprises extensively hydrolyzed protein. In still another embodiment, the protein component of the nutritional composition consists essentially of extensively hydrolyzed protein in order to minimize the occurrence of food allergy. In yet another embodiment, the protein source may be supplemented with glutamine-containing peptides.

Some people exhibit allergies or sensitivities to intact proteins, i.e. whole proteins, such as those in intact cow's milk protein or intact soy protein isolate-based formulas. Many of these people with protein allergies or sensitivities are able to tolerate hydrolyzed protein. Hydrolysate formulas (also referred to as semi-elemental formulas) contain protein that has been hydrolyzed or broken down into short peptide fragments and amino acids and as a result is more easily digested. In people with protein sensitivities or allergies, immune system associated allergies or sensitivities often result in cutaneous, respiratory or gastrointestinal symptoms such as vomiting and diarrhea. People who exhibit reactions to intact protein formulas often will not react to hydrolyzed protein formulas because their immune system does not recognize the hydrolyzed protein as the intact protein that causes their symptoms.

Accordingly, in some embodiments, the protein component of the nutritional composition comprises either partially or extensively hydrolyzed protein, such as protein from cow's milk. The hydrolyzed proteins may be treated with enzymes to break down some or most of the proteins that cause adverse symptoms with the goal of reducing allergic reactions, intolerance, and sensitization. Moreover, the proteins may be hydrolyzed by any method known in the art.

The terms "protein hydrolysates" or "hydrolyzed protein" are used interchangeably herein and refer to hydrolyzed proteins, wherein the degree of hydrolysis is may be from about 20% to about 80%, or from about 30% to about 80%, or even from about 40% to about 60%. The degree of hydrolysis is the extent to which peptide bonds are broken by a hydrolysis method. The degree of protein hydrolysis for purposes of characterizing the hydrolyzed protein component of the nutritional composition is easily determined by one of ordinary skill in the formulation arts by quantifying the amino nitrogen to total nitrogen ratio (AN/TN) of the protein component of the selected formulation. The amino nitrogen component is quantified by USP titration methods for determining amino nitrogen content, while the total nitrogen component is determined by the Kjeldahl method, all of which are well known methods to one of ordinary skill in the analytical chemistry art.

When a peptide bond in a protein is broken by enzymatic hydrolysis, one amino group is released for each peptide bond broken, causing an increase in amino nitrogen. It should be noted that even non-hydrolyzed protein would contain some exposed amino groups. Hydrolyzed proteins will also have a different molecular weight distribution than the non-hydrolyzed proteins from which they were formed.

The functional and nutritional properties of hydrolyzed proteins can be affected by the different size peptides. A molecular weight profile is usually given by listing the percent by weight of particular ranges of molecular weight (in Daltons) fractions (e.g., 2,000 to 5,000 Daltons, greater than 5,000 Daltons).

As previously mentioned, persons who exhibit sensitivity to whole or intact proteins can benefit from consumption of nutritional formulas containing hydrolyzed proteins. Such sensitive persons may especially benefit from the consumption of a hypoallergenic formula.

In some embodiments, the nutritional composition of the present disclosure is substantially free of intact proteins, other than the added lactoferrin. In this context, the term "substantially free" means that the preferred embodiments herein comprise sufficiently low concentrations of intact protein to thus render the formula hypoallergenic. The extent to which a nutritional composition in accordance with the disclosure is substantially free of intact proteins, and therefore hypoallergenic, is determined by the August 2000 Policy Statement of the American Academy of Pediatrics in which a hypoallergenic formula is defined as one which in appropriate clinical studies demonstrates that it does not provoke reactions in 90% of infants or children with confirmed cow's milk allergy with 95% confidence when given in prospective randomized, double-blind, placebo-controlled trials.

Another alternative for pediatric subjects, such as infants, that have food allergy and/or milk protein allergies is a protein-free nutritional composition based upon amino acids. Amino acids are the basic structural building units of protein. Breaking the proteins down to their basic chemical structure by completely pre-digesting the proteins makes amino acid-based formulas the most hypoallergenic formulas available.

In a particular embodiment, the nutritional composition is protein-free and contains free amino acids as a protein equivalent source (in addition to lactoferrin). In this embodiment, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In other embodiments, small amino acid peptides may be included as the protein component of the nutritional composition. Such small amino acid peptides may be naturally occurring or synthesized. The amount of free amino acids in the nutritional composition may vary from about 1 to about 5 g/100 Kcal. In an embodiment, 100% of the free amino acids have a molecular weight of less than 500 Daltons. In this embodiment, the nutritional formulation may be hypoallergenic.

In a particular embodiment of the nutritional composition, the whey:casein ratio of the protein source is similar to that found in human breast milk. In an embodiment, the protein source comprises from about 40% to about 85% whey protein and from about 15% to about 60% casein.

In some embodiments, the nutritional composition comprises between about 1 g and about 7 g of a protein and/or protein equivalent source per 100 Kcal. In other embodiments, the nutritional composition comprises between about 3.5 g and about 4.5 g of protein or protein equivalent per 100 Kcal.

The nutritional composition of the present disclosure may comprise native or modified starches, such as, for example, waxy corn starch, waxy rice starch, corn starch, rice starch, potato starch, tapioca starch, wheat starch or any mixture thereof. Generally, common corn starch comprises about 25% amylose, while waxy corn starch is almost totally made up of amylopectin. Meanwhile, potato starch generally comprises about 20% amylose, rice starch comprises an amylose:amylopectin ratio of about 20:80, and waxy rice starch comprises only about 2% amylose. Further, tapioca starch generally comprises about 15% to about 18% amylose, and wheat starch has an amylose content of around 25%.

In some embodiments, the nutritional composition comprises gelatinized and/or pre-gelatinized waxy corn starch. In other embodiments, the nutritional composition comprises gelatinized and/or pre-gelatinized tapioca starch. Other gelatinized or pre-gelatinized starches, such as rice starch or potato starch may also be used.

Additionally, in some embodiments the nutritional compositions of the present disclosure comprise at least one source of pectin. The source of pectin may comprise any variety or grade of pectin known in the art. In some embodiments, the pectin has a degree of esterification of less than 50% and is classified as low methylated ("LM") pectin. In some embodiments, the pectin has a degree of esterification of greater than or equal to 50% and is classified as high-ester or high methylated ("HM") pectin. In still other embodiments, the pectin is very low ("VL") pectin, which has a degree of esterification that is less than approximately 15%. Further, the nutritional composition of the present disclosure may comprise LM pectin, HM pectin, VL pectin, or any mixture thereof. The nutritional composition may include pectin that is soluble in water. And, as known in the art, the solubility and viscosity of a pectin solution are related to the molecular weight, degree of esterification, concentration of the pectin preparation and the pH and presence of counterions.

Pectins for use herein typically have a peak molecular weight of 8,000 Daltons or greater. The pectins of the present disclosure have a preferred peak molecular weight of between 8,000 and about 500,000, more preferred is between about 10,000 and about 200,000 and most preferred is between about 15,000 and about 100,000 Daltons. In some embodiments, the pectin of the present disclosure may be hydrolyzed pectin. In certain embodiments, the nutritional composition comprises hydrolyzed pectin having a molecular weight less than that of intact or unmodified pectin. The hydrolyzed pectin of the present disclosure can be prepared by any means known in the art to reduce molecular weight. Examples of said means are chemical hydrolysis, enzymatic hydrolysis and mechanical shear. A preferred means of reducing the molecular weight is by alkaline or neutral hydrolysis at elevated temperature. In some embodiments, the nutritional composition comprises partially hydrolyzed pectin. In certain embodiments, the partially hydrolyzed pectin has a molecular weight that is less than that of intact or unmodified pectin but more than 3,300 Daltons.

In some embodiments, the nutritional composition comprises up to about 20% w/w of a mixture of starch and pectin. In some embodiments, the nutritional composition comprises up to about 19% starch and up to about 1% pectin. In other embodiments, the nutritional composition comprises about up to about 15% starch and up to about 5% pectin. In still other embodiments, the nutritional composition comprises up to about 18% starch and up to about 2% pectin. In some embodiments the nutritional composition comprises between about 0.05% w/w and about 20% w/w of a mixture of starch and pectin. Other embodiments include between about 0.05% and about 19% w/w starch and between about 0.05% and about 1% w/w pectin. Further, the nutritional composition may comprise between about 0.05% and about 15% w/w starch and between about 0.05% and about 5% w/w pectin.

In some embodiments, the nutritional composition comprises at least one additional carbohydrate, that is, a carbohydrate component provided in addition to the aforementioned starch component. Additional carbohydrate sources can be any used in the art, e.g., lactose, glucose, fructose, corn syrup solids, maltodextrins, sucrose, starch, rice syrup solids, and the like. The amount of the additional carbohydrate component in the nutritional composition typically can vary from between about 5 g and about 25 g/100 Kcal. In some embodiments, the amount of carbohydrate is between about 6 g and about 22 g/100 Kcal. In other embodiments, the amount of carbohydrate is between about 12 g and about 14 g/100 Kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

Particular embodiments of the present compositions include lactose as a carbohydrate source. In one particular embodiment, the additional carbohydrate component of the nutritional composition is comprised of 100% lactose. In another embodiment, the additional carbohydrate component comprises between about 0% and 60% lactose. In another embodiment, the additional carbohydrate component comprises between about 15% and 55% lactose. In yet another embodiment, the additional carbohydrate component comprises between about 20% and 30% lactose. In these embodiments, the remaining source of carbohydrates may be any carbohydrate known in the art. In an embodiment, the carbohydrate component comprises about 25% lactose and about 75% corn syrup solids.

In some embodiments the nutritional composition comprises sialic acid. Sialic acids are a family of over 50 members of 9-carbon sugars, all of which are derivatives of neuroaminic acid. The predominant sialic acid family found in humans is from the N-acetylneuraminic acid sub-family. Sialic acids are found in milk, such as bovine and caprine. In mammals, neuronal cell membranes have the highest concentration of sialic acid compared to other body cell membranes. Sialic acid residues are also components of gangliosides.

If included in the nutritional composition, sialic acid may be present in an amount from about 0.5 mg/100 Kcals to about 45 mg/100 Kcal. In some embodiments sialic acid may be present in an amount from about 5 mg/100 Kcals to about 30 mg/100 Kcals. In still other embodiments, sialic acid may be present in an amount from about 10 mg/100 Kcals to about 25 mg/100 Kcals.

The present nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans.Yakugaku Zasshi. 2000; 120: 413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalties, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, Saccharomyces cerevisiae, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition of the present disclosure comprises β-glucan. In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

In some embodiments, the amount of β-glucan present in the composition is at between about 0.010 and about 0.080 g per 100 g of composition. In other embodiments, the nutritional composition comprises between about 10 and about 30 mg β-glucan per serving. In another embodiment, the nutritional composition comprises between about 5 and about 30 mg β-glucan per 8 fl. oz. (236.6 mL) serving. In other embodiments, the nutritional composition comprises an amount of β-glucan sufficient to provide between about 15 mg and about 90 mg β-glucan per day. The nutritional composition may be delivered in multiple doses to reach a target amount of β-glucan delivered to the subject throughout the day.

In some embodiments, the amount of β-glucan in the nutritional composition is between about 3 mg and about 17 mg per 100 Kcal. In another embodiment the amount of β-glucan is between about 6 mg and about 17 mg per 100 Kcal.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

The nutritional composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E (α-tocopherol, α-tocopherol acetate, α-tocopherol succinate, α-tocopherol nicotinate, α-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional compositions of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 µm to 1500 µm, more preferably in the range of 10 µm to 300 µm.

If the nutritional composition is in the form of a ready-to-use product, the osmolality of the nutritional composition may be between about 100 and about 1100 mOsm/kg water, more typically about 200 to about 700 mOsm/kg water.

Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 7 g/100 Kcal. The amount of protein typically can vary from about 1 to about 7 g/100 Kcal. The amount of carbohydrate typically can vary from about 6 to about 22 g/100 Kcal.

In an embodiment, the nutritional composition(s) of the present disclosure comprises an effective amount of choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes an effective amount of choline, which is about 20 mg choline per 8 fl. oz. (236.6 mL) serving to about 100 mg per 8 fl. oz. (236.6 mL) serving.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The present disclosure also provides maternal supplements comprising PE, SM, LF and DHA. The maternal supplement is useful for pregnant women, in which brain development, particularly neuronal maturation, of the fetus is enhanced by administration of the supplement to a pregnant woman. Alternatively, a nutritional supplement may be provided to a breastfeeding mother to support neuronal maturation in a breastfeeding infant.

The present disclosure further provides a method for providing nutritional support to a subject. The method includes administering to the subject an effective amount of the nutritional composition of the present disclosure.

The nutritional composition may be expelled directly into a subject's intestinal tract. In some embodiments, the nutritional composition is expelled directly into the gut. In some embodiments, the composition may be formulated to be consumed or administered enterally under the supervision of a physician and may be intended for the specific dietary management of a disease or condition, such as celiac disease and/or food allergy, for which distinctive nutritional requirements, based on recognized scientific principles, are established by medical evaluation.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

In some embodiments, the nutritional composition may be delivered to an infant from birth until a time that matches full-term gestation. In some embodiments, the nutritional composition may be delivered to an infant until at least about three months corrected age. In another embodiment, the nutritional composition may be delivered to a subject as long as is necessary to correct nutritional deficiencies. In yet another embodiment, the nutritional composition may be delivered to an infant from birth until at least about six months corrected age. In yet another embodiment, the nutritional composition may be delivered to an infant from birth until at least about one year corrected age.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

In certain embodiments, the nutritional composition is hypoallergenic. In other embodiments, the nutritional composition is kosher. In still further embodiments, the nutritional composition is a non-genetically modified product. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

In some embodiments, the disclosure is directed to a staged nutritional feeding regimen for a pediatric subject, such as an infant or child, which includes a plurality of different nutritional compositions according to the present disclosure. Each nutritional composition comprises a hydrolyzed protein, at least one pre-gelatinized starch, and at least one pectin. In certain embodiments, the nutritional compositions of the feeding regimen may also include a source of long chain polyunsaturated fatty acid, at least one prebiotic, an iron source, a source of β-glucan, vitamins or minerals, lutein, zeaxanthin, or any other ingredient described hereinabove. The nutritional compositions described herein may be administered once per day or via several administrations throughout the course of a day.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

EXAMPLES

Example 1

Cortical cells were grown on multi-well microelectrode arrays (MEAs) and treated with 10 different experimental series, including different combinations of test agents (PE, SM, LF and DHA) and the activity was recoded at 4 different time points during the 4 weeks of functional neuronal maturation Cells growing on glass slides were treated in parallel for morphological and cell population analysis. These experiments aimed to elucidate whether the test compounds affect the functional and morphological neuronal maturation in vivo (see FIG. 1).

All experiments were performed according to the standard operating protocols (SOPs): "SOP Preparation Frontal Cortex Mouse—Serum," "SOP Solutions for Neuronal Cell Culture," "SOP Cleaning and Substrate Preparations of MEAs," "SOP Feeding neuronal cell culture," "SOP Cell culture preparation MEAs," "SOP Plexon Recording," "SOP Plexon Data Analysis."

Microelectrode Array Neurochips: THE MEA neurochips were provided by the Center for Network Neuroscience (CNNS) at the University of North Texas. These 5×5 $cm^2$ glass chips have a dual recording matrix with 32 passive electrodes per matrix and indium tin oxide conductors. The hydrophobic insulation material surface was activated by a brief butane flame pulse through a stainless steel mask. Thus, cell attachment on a confined adhesive region (5 mm diameter centered on the electrode array) is ensured. The activated surface regions were coated with poly-D-lysine (25 microgram/mL; 30-70 kD) and incubated overnight. The surfaces were then treated with laminin (16 microgram/mL) for three hours right before preparation.

Primary cell culture for MEA recordings: In brief, frontal cortex tissue was harvested from embryonic day 15 chr NMRI mice. Mice were sacrificed by cervical dislocation according to the German Animal Protection Act § 4. Cultures on MEAs were incubated at 37° C. in a 10% $CO_2$ atmosphere until ready for use, which usually is four weeks to three months after seeding. Culture media were replenished two times a week by a ⅓ exchange with fresh DMEM containing 10% heat inactivated horse serum. If required, the developing cultures were treated with the mitosis inhibitor 5-fluoro-2'-deoxyuridine (25 microM) and uridine (63 microM).

Chronic Treatment of Cultures Growing on Multiwell MEAs: The cultures were prepared as described above. On day 4 in vitro the treatment started and the phospholipids were added to the fresh culture medium. Since the phospholipid concentration is assumed to be reduced to zero during the time between the medium changes, the complete concentration of the phospholipids was adjusted in the culture well during every medium change. The concentrations are set forth in Table 1:

|           | Vehicle (temporal accumulation) |         |       |        |        |        |
|-----------|--------------------------------|---------|-------|--------|--------|--------|
| treatment | Ethanol %                      | DMSO %  | DHA   | PE     | LTF    | SPH    |
| 1         | 0.004                          | 0.040   | 20 μM | 100 nM | 300 nM | 100 nM |
| 2         | 0.006                          | 0.067   | 20 μM | 100 nM | 300 nM | 100 nM |
| 3         | 0.008                          | 0.084   | 20 μM | 100 nM | 300 nM | 100 nM |

| | Vehicle (temporal accumulation) | | | | | |
|---|---|---|---|---|---|---|
| treatment | Ethanol % | DMSO % | DHA | PE | LTF | SPH |
| 4 | 0.009 | 0.096 | 20 µM | 100 nM | 300 nM | 100 nM |
| 5 | 0.010 | 0.104 | 20 µM | 100 nM | 300 nM | 100 nM |
| 6 | 0.010 | 0.110 | 20 µM | 100 nM | 300 nM | 100 nM |
| 7 | 0.011 | 0.113 | 20 µM | 100 nM | 300 nM | 100 nM |
| 8 | 0.011 | 0.115 | 20 µM | 100 nM | 300 nM | 100 nM |

Multichannel Recording: After establishing a stable activity pattern after 4 weeks, the neuronal networks on MEA chips are employed for substance testing. For this study, cultures between 25 and 38 days in vitro were used. For extracellular recording, MEA neurochips were placed into sterilized constant-bath recording chambers and maintained at 37° C. Recordings were made in DMEM/10% heat inactivated horse serum. The pH was maintained at 7.4 with a continuous stream of filtered humidified airflow with 10% $CO_2$. Sets of preamplifiers were positioned to either side of the recording chamber. Recording was performed with the multichannel acquisition processor system, a computer-controlled 64-channel amplifier system (Plexon, Inc., Dallas, Tex., USA) providing programmable amplification, filtering, switching, and digital signal processing of microelectrode signals. The total system gain used was 10K with a simultaneous 4040 kHz sampling rate. The signals routinely recorded by these neurochips are located in a range of 15-1800 $\mu V$. The multichannel signal acquisition system delivered single neuron spike data. Spike identification and separation were accomplished with a template-matching algorithm in real time. This allows the extracellular recording of action potentials from a maximum of 256 neurons simultaneously. The action potentials, or "spikes", were recorded in spike trains and clustered in so-called bursts. Bursts were quantitatively described via direct spike train analysis using the program NeuroExplorer (Plexon Inc., Dallas, Tex., USA) and in-house programs. Bursts were defined by the beginning and end of short spike in-vents. Maximum spike intervals defining the start of a burst were 40 ms and maximum intervals to end a burst were 200 ms.

Multiparametric Data Analysis: The high content analysis of the network activity patterns provides a multiparametric description characterizing the activity in four categories: general activity, burst structure, synchronicity and oscillatory behavior. From the spike trains, a total of 200 activity-describing spike train parameters for these four categories were determined. We normalized all compound-induced network activity to the related spontaneous native activity, set at 100% for each experiment. Values were derived from 60 second bin data taken from a 30 minutes span after a 30 min stabilization of activity. The data report includes concentration response curves of all test compounds and vehicle controls on a core set of 16 parameters describing the four categories general activity, burst structure as well as the oscillatory and synchronicity behavior. These parameters deliver most of the information relating to the influence of the test agents on the overall network activity. Results (parameter values) are expressed as mean±SEM of independent networks. The absolute parameter distributions were tested for normality. The statistical significance of a compound-induced effect on native cortical activity was assessed by the paired Student's t-test, the effects of the compound versus vehicle-induced effects were assessed by the unpaired Student's t-test. Statistical comparisons were performed separately for each time point: $p<0.05$ was considered statistically significant.

Primary Cell culture for immunocytochemistry and Fluorescence staining: The chronically treated cultures were grown on 24-well plates on 13 mm glass cover slides and cultured with PNGM medium including 5% FCS and gentamycin+ampicillin. The cells were treated 2× per week during ⅓ medium exchange. The complete concentration of phospholipids was replenished every time.

Immunocytochemistry and Fluorescence staining: These 24 well-plate cultures were analyzed by immunocytochemistry, fluorescence microscopy and semiautomatic quantitative image analysis at 7, 14, 21, and 28 days. The cells were initially washed with PBS and fixed with 4% PFA for 30 min, followed by addition of a PBS-based blocking solution containing 1% BSA, 2% goat serum and 0.05% TWEEN20, and incubated with primary antibodies neuronal soma with anti-Hu C/D (1:500; neuronal-specific RNA-stabilizing protein present in neuronal cell bodies, Life technologies, Germany) co-labeled with Alexa488 (1:500, Life technologies, Germany), synapses with anti-synapsin-1 (1:200; Cell Signaling, Houston, USA) co-labeled with Alexa488 (1:500), and a selection of samples was co-labeled for neurites with anti-tubulin beta-III (1:750; Sigma-Aldrich, Germany) also co-labeled with Alexa488 (1:500); and nuclei with the DNA-dye Hoechst/Bisbenzimide (1 $\mu$g/ml; SigmaAldrich, Taufkirchen, Germany). Cortical networks were embedded with Prolong anti-fade gold (Invitrogen, Darmstadt, Germany) and images acquired with an upright fluorescence microscope (Nikon Eclipse TE200, NikonAG, Tokyo, Japan).

Image analysis: These images were analyzed by semiautomatic image quantification tools (MS Excel macrobased in house analyses; ImageJ, Rawak Software, NIH, USA). The following parameters were quantified per image and normalized to the respective control per independent culture preparation, means and SEM's were calculated afterwards: a) cell number: absolute number of nuclei/field (marker: nuclear staining, automatic counting after image processing (binary, watershed); b) neuronal number: absolute number of neuronal soma I field (marker: HuC/Dpositive objects, manual and semi-automatic counting); c) % neurons: number of neurons/field normalized by total number of cells/field; d) synapse number: absolute number of synapse punctae/field; automatic analysis (automatic analysis, local automatic threshold setting); e) synaptic density: synapse number/image normalized by neuronal number per image.

Description of test compounds: DHA (Sigma Aldrich, #D2534, Lot SLBB6915V), CAS number 6217-54-5 Mol. Mass [g·mol−1]: 328.49; Vehicle: DMSO (Sigma Aldrich, #472301, Lot RNBB9706); Aqua (BRAUN, #0123, Lot 132148001); Solubilization procedure: Stock solution: 100 mM in 100% DMSO, Storage: −20° C. PE (Biotrend #1069, Lot 23759 CAS number: 90989-93-8 Mol. Mass [g·mol−1]: 744; Vehicle: Ethanol (Sigma-Aldrich, Lot RNBB9706); Aqua (BRAUN, #0123, Lot 132148001. Solubilization procedure: Stock solution: 67 mM in 10% DMSO. Storage: −20° C. SM (Biotrend, #1051, Lot 23149) CAS number 85187-10-6, Mol. Mass [g·mol−1]: 815, Vehicle: Ethanol (Sigma-Aldrich, Lot RNBB9706); Aqua (BRAUN, #0123, Lot 132148001). Solubilization procedure: Stock solution: 13 mM in 100% Ethanol, Storage: −20° C. LF (glanbia, Lot 20303491) Mol. Mass [g·mol−1]: 80000, Vehicle: Ethanol (Sigma-Aldrich, Lot RNBB9706); Aqua (BRAUN, #0123, Lot 132148001). Solubilization procedure: Stock solution: 1 mM in 100% Aqua, Storage: −20° C.

Figure 2:
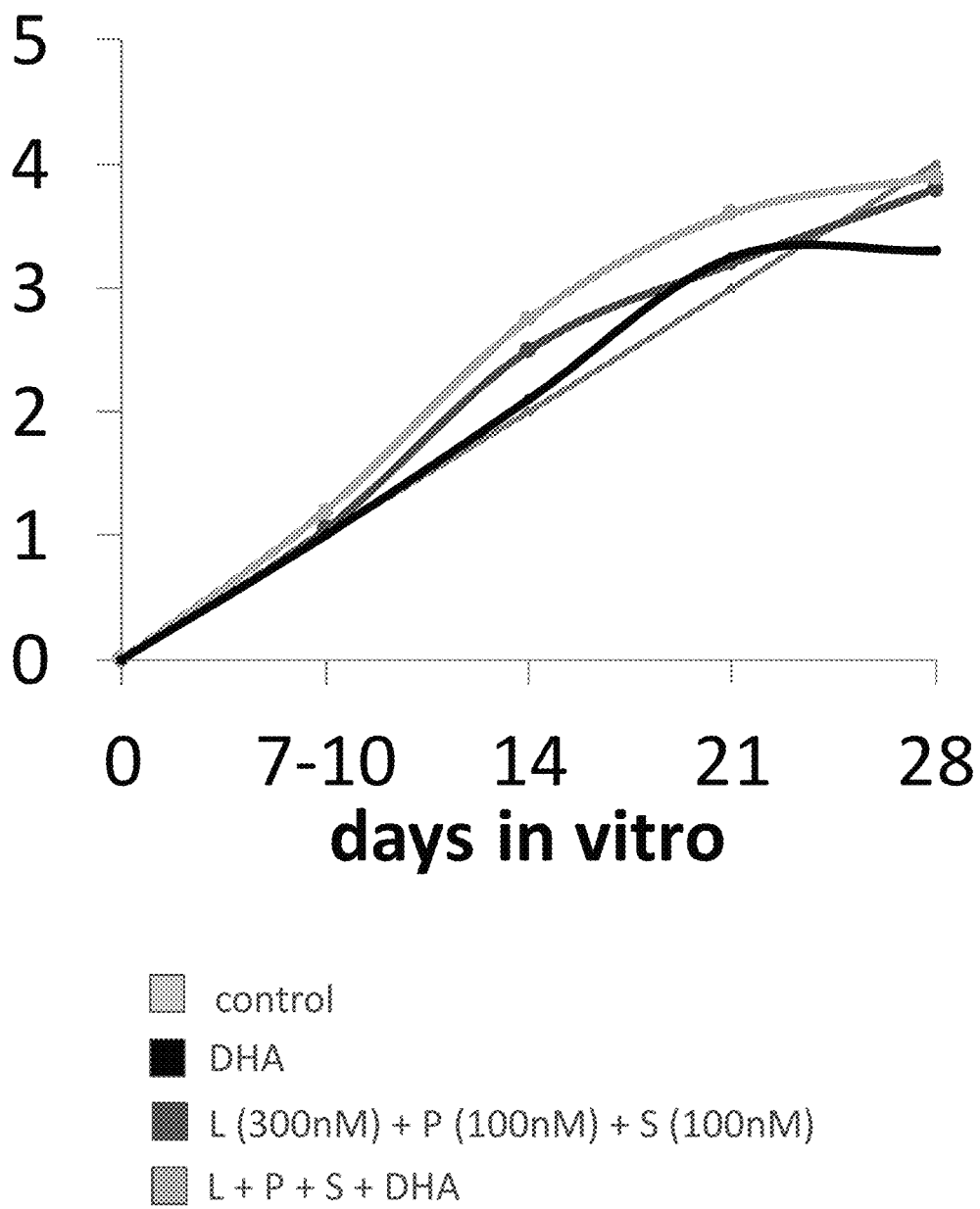
FIG. 2 depicts a graphical sketch summarizing the effects of LF, SM, PE, DHA, and various combinations thereof, on functional neuronal maturation on embryonic mouse cortical cells over a 28 day period.

Quantification of functional and morphological chronic effects of test compounds and their combinations on primary neuronal networks. It was to investigate how a repeated treatment of 2× per week with the different compounds affect the functional electrophysiological development, i.e. maturation, of cortical neuronal networks which grow on MEAs. The respective cultures were repeatedly recorded at 4 time points during 4 weeks maturation: 7-10, 14, 21 and 28 days in vitro (div). FIG. 2 qualitatively summarizes the effects of DHA, LF, PE, SM; the combination of LF+PE+SM and all groups in combination with DHA. In summary, In conclusion the complete combination of LF+PE+SM and DHA shows the strongest accelerative effects on early neuronal development but does not exhibit a developmental halt at later stages, as seen for DHA alone or in combination with LF and PE, or for SPM alone.

Figure 3:
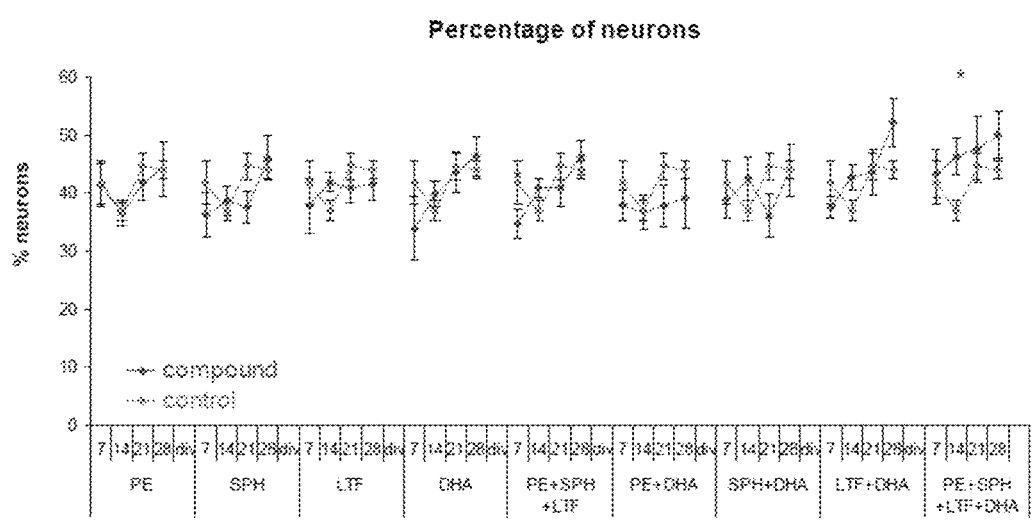
FIG. 3 is a graph depicting the percentage of neurons in the embryonic mouse cortical cell cultures during a 28 day period of treatment with various combinations of PE, SM, LF and DHA compared to a control.

The repeated treatment with LF+PE+SM+DHA affects development of neuronal network morphology: The recorded networks were fixed after the final 28 div recording and immunostained for neuronal markers. Images were taken and the cell neuronal numbers quantified by semi-automatic image analyses. In summary, the results show that in comparison to control (FIG. 3) the complete combination of LF, PE, SM and DHA is able to increase the neuronal percentage, especially at div 14.

Overall conclusion and summary: The results suggest that PE, SM, LF and combinations with DHA acutely affect neuronal network activity in vitro. The complete combination of SM+LF+PE+DHA accelerated the 4-weeks neuronal maturation process by approximately one week without inhibitory effects at later stages, indicating a surprising synergistic effect of these compounds. Parallel morphological analysis of these experiments showed numerically increased neuronal populations in the LF+DHA combination and the complete mixture of all four compounds. SM is also able to increase the synaptic density.

Example 2

An exemplary formulation in accordance with the present disclosure is as follows:

| Nutrient | Unit | Per 100 Kcal |
|---|---|---|
| Protein | g | 2.1 |
| Fat | g | 5.3 |
| Enriched whey protein concentrate | g | 0.74 |
| Linoleic Acid | mg | 810 |
| Alpha-Linolenic Acid | mg | 71 |
| Docosahexaenoic Acid | mg | 17.8 |
| Arachidonic Acid | mg | 36 |
| Carbohydrates | g | 11.2 |
| GOS | g | 0.31 |
| Polydextrose | g | 0.31 |
| Vitamin A | μg | 84 |
| Vitamin D | μg | 1.55 |
| Vitamin E | mg | 1.27 |
| Vitamin K | μg | 7.2 |
| Thiamin | μg | 85 |
| Riboflavin | μg | 170 |
| Vitamin B6 | μg | 60 |
| Vitamin B12 | μg | 0.31 |
| Niacin | μg | 660 |
| Folic Acid | μg | 18 |
| Pantothenic Acid | μg | 570 |
| Biotin | μg | 2.7 |
| Vitamin C | mg | 18 |
| Sodium | mg | 28 |
| Potassium | mg | 110 |
| Chloride | mg | 65 |
| Calcium | mg | 79 |
| Phosphorus | mg | 48 |
| Magnesium | mg | 8 |
| Iodine | μg | 17 |
| Iron | mg | 1 |
| Copper | μg | 65 |
| Zinc | mg | 0.8 |
| Manganese | μg | 18 |
| Selenium | μg | 2.7 |
| Choline | mg | 24 |
| Inositol | mg | 8.5 |
| Carnitine | mg | 2 |
| Taurine | mg | 6 |
| Total Nucleotides | mg | 3.1 |

Example 3

Another exemplary formulation in accordance with the present disclosure is as follows:

| Nutrient | Unit | Per 100 Kcal |
|---|---|---|
| Protein | g | 3.3 |
| Fat | g | 4.1 |
| Enriched whey protein concentrate | g | 0.74 |
| Linoleic Acid | mg | 640 |
| Alpha-Linolenic Acid | mg | 56 |
| Docosahexaenoic Acid | mg | 17.3 |
| Arachidonic Acid | mg | 35 |
| Carbohydrates | g | 12.8 |
| GOS | g | 0.35 |
| Polydextrose | g | 0.35 |
| Vitamin A | μg | 90 |
| Vitamin D | μg | 1.4 |
| Vitamin E | mg | 1.14 |
| Vitamin K | μg | 8 |
| Thiamin | μg | 80 |
| Riboflavin | μg | 200 |
| Vitamin B6 | μg | 70 |
| Vitamin B12 | μg | 0.5 |
| Niacin | μg | 700 |
| Folic Acid | μg | 16 |
| Pantothenic Acid | μg | 650 |
| Biotin | μg | 3 |
| Vitamin C | mg | 20 |
| Sodium | mg | 46 |
| Potassium | mg | 150 |
| Chloride | mg | 94 |
| Calcium | mg | 110 |
| Phosphorus | mg | 65 |
| Magnesium | mg | 9.5 |
| Iodine | μg | 22 |
| Iron | mg | 1.25 |
| Copper | μg | 68 |

-continued

| Nutrient | Unit | Per 100 Kcal |
|---|---|---|
| Zinc | mg | 0.76 |
| Manganese | µg | 17.8 |
| Selenium | µg | 2.5 |
| Choline | mg | 24 |
| Inositol | mg | 7 |
| Taurine | mg | 4.3 |
| Total Nucleotides | mg | 4 |
| Lactoferrin | g | 0.09 |

Example 4

Yet another exemplary formulation in accordance with the present disclosure is as follows:

| Nutrient | Unit | Per 100 Kcal |
|---|---|---|
| Protein | g | 3.4 |
| Fat | g | 3.7 |
| Enriched whey protein concentrate | g | 0.62 |
| Linoleic Acid | mg | 390 |
| Alpha-Linolenic Acid | mg | 38 |
| Docosahexaenoic Acid | mg | 13.9 |
| Carbohydrates | g | 13.5 |
| Dietary Fiber (Prebiotics) | g | 0.7 |
| GOS | g | 0.35 |
| Polydextrose | g | 0.35 |
| Beta-Glucan | mg | 4.9 |
| Vitamin A | µg | 97 |
| Vitamin D | µg | 1.5 |
| Vitamin E | mg | 1.11 |
| Vitamin K | µg | 7.8 |
| Thiamin | µg | 133 |
| Riboflavin | µg | 122 |
| Vitamin B6 | µg | 200 |
| Vitamin B12 | µg | 0.78 |
| Niacin | µg | 1220 |
| Folic Acid | µg | 33 |
| Pantothenic Acid | µg | 560 |
| Biotin | µg | 2.4 |
| Vitamin C | mg | 17.8 |
| Calcium | mg | 139 |
| Phosphorus | mg | 94 |
| Magnesium | mg | 13.9 |
| Sodium | mg | 51 |
| Potassium | mg | 165 |
| Chloride | mg | 111 |
| Iodine | µg | 21 |
| Iron | mg | 1.33 |
| Zinc | mg | 0.84 |
| Manganese | µg | 62 |
| Copper | µg | 83 |
| Taurine | mg | 4.4 |
| Choline | mg | 22 |
| Lactoferrin | g | 0.07 |

Although preferred embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the preferred versions contained therein.

What is claimed is:

1. A method for promoting neuronal maturation in a fetus comprising:
   administering to a female subject pregnant with the fetus a maternal nutritional supplement comprising:
   about 3 mg/100 Kcal to about 50 mg/100 Kcal of phosphatidylethanolamine;
   about 0.15 mg/100 Kcal to about 75 mg/100 Kcal of sphingomyelin;
   about 10 mg/100 Kcal to about 200 mg/100 Kcal of lactoferrin;
   about 0.015 g/100 Kcal to about 0.15 g/100 Kcal of a prebiotic composition, wherein the prebiotic composition comprises polydextrose, galactooligosaccharide or a combination thereof; and
   about 5 mg/100 Kcal to about 75 mg/100 Kcal of docosahexaenoic acid.

2. The method of claim 1, wherein the maternal nutritional supplement further comprises up to about 7 g/100 Kcal of a fat or lipid source; and up to about 5 g/100 Kcal of a protein source.

3. The method of claim 1, wherein polydextrose and galactooligosaccharide comprise at least about 20% of the prebiotic composition.

4. The method of claim 1, wherein the maternal nutritional supplement further comprises *Lactobacillus rhamnosus* GG.

5. The method of claim 1, wherein the maternal nutritional supplement further comprises arachidonic acid, wherein arachidonic acid and docosahexaenoic acid are present in a weight ratio ranging from about 1:3 to 9:1.

6. The method of claim 1, wherein the maternal nutritional supplement further comprises human milk oligosaccharides.

7. The method of claim 1, wherein the phosphatidylethanolamine and sphingomyelin are provided by a milk fat globular membrane-enriched ingredient.

8. The method of claim 1, wherein the maternal nutritional supplement further comprises a carbohydrate source comprising lactose.

9. A method for promoting neuronal maturation in an infant comprising:
   a) administering to a lactating female subject a nutritional supplement comprising:
      about 3 mg/100 Kcal to about 50 mg/100 Kcal of phosphatidylethanolamine;
      about 0.15 mg/100 Kcal to about 75 mg/100 Kcal of sphingomyelin;
      about 10 mg/100 Kcal to about 200 mg/100 Kcal of lactoferrin;
      about 0.015 mg/100 Kcal to about 0.15 g/100 Kcal of a prebiotic composition, wherein the prebiotic composition comprises polydextrose, galactooligosaccharide or a combination thereof; and
      about 5 mg/100 Kcal to about 75 mg/100 Kcal of docosahexaenoic acid; and
   b) administering breast milk from the lactating female to the infant.

10. The method of claim 9, wherein the nutritional supplement further comprises up to about 7 g/100 Kcal of a fat or lipid source; and up to about 5 g/100 Kcal of a protein source.

11. The method of claim 9, wherein polydextrose and galactooligosaccharide comprise at least about 20% of the prebiotic composition.

12. The method of claim 9, wherein the nutritional supplement further comprises *Lactobacillus rhamnosus* GG.

13. The method of claim 9, wherein the nutritional supplement further comprises arachidonic acid, wherein arachidonic acid and docosahexaenoic acid are present in a weight ratio ranging from about 1:3 to 9:1.

14. The method of claim 9, wherein the nutritional supplement further comprises human milk oligosaccharides.

15. The method of claim 9, wherein the phosphatidylethanolamine and sphingomyelin are provided by a milk fat globular membrane-enriched ingredient.

16. The method of claim 9, wherein the nutritional supplement further comprises a carbohydrate source comprising lactose.

* * * * *